United States Patent [19]
Gordon

[11] Patent Number: 5,681,586
[45] Date of Patent: Oct. 28, 1997

[54] ENZYME-MODIFIED SOY AND SOY/CASEIN COMBINATION HEALING COMPOSITIONS

[76] Inventor: Arthur L. Gordon, 109 Phaeton Dr., Wheeling, Ill. 60090

[21] Appl. No.: 660,082

[22] Filed: Jun. 3, 1996

Related U.S. Application Data

[63] Continuation-in-part of Ser. No. 346,693, Nov. 20, 1994, abandoned, which is a continuation-in-part of Ser. No. 202,387, Feb. 28, 1994, abandoned, which is a continuation-in-part of Ser. No. 981,118, Nov. 23, 1992, abandoned, which is a continuation-in-part of Ser. No. 327,743, Mar. 23, 1989, Pat. No. 5,166,132.

[51] Int. Cl.⁶ .................................................. A61K 35/20
[52] U.S. Cl. .................... 424/535; 424/80; 424/195.1; 424/DIG. 13; 514/2; 514/21; 530/360; 530/361; 530/832; 530/833
[58] Field of Search ................. 514/2, 21; 424/80, 424/DIG. 13, 535, 195.1; 530/360, 361, 832, 833

[56] References Cited

U.S. PATENT DOCUMENTS

| | | | |
|---|---|---|---|
| 3,558,770 | 1/1971 | Gordon | 424/535 |
| 4,883,659 | 11/1989 | Goodman et al. | 424/78 |
| 4,971,800 | 11/1990 | Chess et al. | 424/449 |
| 5,051,260 | 9/1991 | Chess et al. | 424/449 |

*Primary Examiner*—Jean C. Witz
*Attorney, Agent, or Firm*—Kajane McManus

[57] ABSTRACT

A pharmaceutical composition comprising an improved modified protein sol is used for treating and enhancing the healing of arthritis and cutaneous acne. Prior to being modified, a protein is solubilized and neutralized by an alkali solution containing a molar weight percent ratio of 95:5 KOH/NaOH. Neutralization is allowed to continue for about 5 minute, allowing for complete neutralization of the protein. The neutralized protein is then hydrolyzed by enzymatic digestion. The improved modified protein sol may be then mixed with stabilizing and preserving agents, such as polyvinyl pyrrolidone, if desired. Uses for the improved modified protein composition includes treatment of arthritis and cystic acne.

6 Claims, No Drawings

ENZYME-MODIFIED SOY AND SOY/CASEIN COMBINATION HEALING COMPOSITIONS

CROSS-REFERENCE TO RELATED APPLICATION

This patent application is a continuation-in-part of U.S. patent application Ser. No. 346,693 filed on Nov. 20, 1994, abandoned, which is a continuation-in-part of U.S. patent application No. 08/202,387 filed Feb. 28, 1994, abandoned, which is a continuation-in-part of U.S. patent application No. 07/981,118, filed Nov. 23, 1992, abandoned, which is a continuation in part of the U.S. patent application No. 07/327,743, filed Mar. 23, 1989, and issued as U.S. Pat. No. 5,166,132.

BACKGROUND OF THE INVENTION

1. Field of the Invention

This present invention relates generally to pharmaceutical compositions comprised of proteins and related polypeptides used to heal arthritis and cutaneous maladies, such as cystic acne.

2. Description of the Prior Art

Some of the healing properties of colloidal compositions containing casein or polyvinyl pyrrolidone (PVP) have been long known. Casein, which is a series of related phosphoproteins, occurs naturally in bovine milk to the extent of about 3%. Casein is commonly produced through various means of precipitating the casein curd from the milk. One of the unique features of casein is that it contains all of the amino acids found in living tissue. When degraded with zinc acetate, casein has been used as a burn ointment.

PVP was originally developed in Germany during World War II as a blood plasma extender, but it currently has numerous applications in the pharmaceutical, cosmetic, and food industries. PVP has been found to render various toxic materials less active due to its ability to form larger complexes with these toxic materials.

Some of these healing and related properties of casein and PVP were brought together in research conducted which culminated in U.S. Pat. No. 5,166,132. In this U.S. Patent is disclosed casein neutralized with potassium hydroxide (KOH) for 10 to 15 minutes and then hydrolyzed with a proteolytic enzyme or protease in a crystalline form, creating polypeptides. The enzyme-modified casein is freeze dried, pulverized, reconstituted, and mixed with suspending, stabilizing, and preservative agents, such as PVP. This enzyme-modified casein sol was found to be very effective as a wrinkle remover and a healing agent in the treatment of wounds resulting from traumatic injuries; healing such wounds, for example, in 4 to 5 days.

Since 1971, much of the focus in wound healing, beyond antiseptics, bandages or skin grafts, has been in synthesizing proteins known as growth factors. A protein consists of a long chain of amino acids linked from the amino group of one amino acid to the carboxyl group of the next. Each link or peptide linkage is formed as a result of removing one water molecule from each pair of amino acids or dipeptides; i.e., an OH from the carboxyl terminus of one amino acid and an H from the amino terminus of the second amino acid. With genetic engineering techniques, scientists have been able to produce some of these naturally occurring growth factor proteins, which have potential in the treatment of wounds resulting from traumatic injuries or burns.

As effective as the previously proposed pharmaceutical casein composition is, one disadvantage found is the tackiness or stickiness of the sol which creates an unaesthetic appearance and feeling for the user. Further, it has been found that a simplified method using soy and a soy/casein combination produces a functional composition as well.

SUMMARY OF THE INVENTION

Accordingly, it is a general object of the present invention to provide an improved protein composition for pharmaceutical use and a simplified process for preparation of the same.

It is a more specific object of the present invention to provide a pharmaceutical composition containing soy or soy/casein polypeptides and related proteinaceous materials that is an effective healing agent in the treatment of arthritis and cutaneous maladies, such as cystic acne.

It is a further object of the present invention to provide a pharmaceutical composition to promote healing that can be produced simply, quickly and economically.

Additional objects, advantages and novel features of the invention shall be, in part, set forth in the description that follows, in part will become apparent to those skilled in the art upon examination of the following specification or may be learned by the practice of the invention.

To achieve the foregoing and other objects, and in accordance with the purpose of the present invention, as embodied as described herein, the pharmaceutical composition of this invention may comprise soy protein or a soy/casein protein combination. When the combination soy/casein composition is chosen it must be solubilized and neutralized, by an alkali solution, said alkali solution preferably comprising potassium hydroxide (KOH) in conjunction with sodium hydroxide (NaOH) at a molecular weight percentage ratio of KOH to NaOH of 95:5. The combined soy/casein sol is allowed to equilibrate with the alkali solution of the protein, i.e., in the range of 5 minutes.

Such a neutralization step is not necessary when soy protein is used alone, as the soy sol has a Ph of approximately 7.0.

Once the protein is completely neutralized, the peptide linkages become more accessible and may be readily cleaved by proteases, which function by adding a water molecule back to the peptide linkage in the process of hydrolysis. Hydrolysis may be achieved through a protease such as trypsin or papain. To the protein sol a protease is added thus initiating hydrolysis of the protein, and digestion is continued for a time sufficient to achieve a preferred level of hydrolysis. A partial hydrolysis of the protein is preferred. The degree of neutralization of the protein, the quantity of the protein, the quantity of the protease, and the duration of the hydrolysis are all critical parameters when attempting to partially cleave the protein, thereby producing polypeptides having particular weight ratios of protein nitrogen to amino nitrogen. Experimental data suggests that, upon complete neutralization of the protein, the addition of 10 ml of protease having a concentration of 10 mg/ml to approximately 150 grams of the protein sol and digesting for 3 to 5 minutes will lead to the desired result. During digestion the mixture is heated, such that when the time sufficient to achieve the desired level of hydrolysis has expired, the mixture has been heated to the inactivation temperature of the protease. The resultant improved enzyme-modified protein or protein combination may be, but does not have to be, mixed with suspending, stabilizing, and preservative agents, such as PVP.

The improved enzyme-modified soy protein and combined soy/casein protein provides an improved composition for topical pharmaceutical use. It has demonstrated significantly less tackiness while yet affording improved healing. In addition, initial studies and trials have shown that tissue regeneration during treatment has been found to effect healing of cutaneous acne. Further, when applied topically, the soothing and healing effects of this improved enzyme-modified protein extends to arthritis.

DETAILED DESCRIPTION OF THE PREFERRED EMBODIMENT

This invention includes a process for the preparation of an improved enzyme hydrolyzed soy and combined soy/casein protein, which demonstrate desired healing rates while eliminating tackiness associated with pure casein.

This pharmaceutical composition can be left and used as a sol. The final step is to then pasteurize the sol, thus forming an improved enzyme-modified soy composition.

A stabilizing agent, such as PVP may be added. Despite the known healing properties of PVP it was found that the improved enzyme-modified soy displayed significant cutaneous wound healing rates, even without the addition of PVP. This result was not expected from any data previously available. It was known that the most important component contributing to the healing efficiency was the enzyme-modified protein; however, there appears to be no significant reduction in healing efficiency with the improved enzyme-modified soy alone, without any added PVP.

The protease used may be either trypsin or papain. Each enzyme is prepared as follows:

To prepare the papain enzyme, 0.2 grams of papain obtained from Baxter Labs, Deerfield, Ill., is diluted to 40 milliliters with distilled $H_2O$. 10 milliliters (0.05 grams of papain) is used in each application defined below.

To prepare the trypsin enzyme 0.5 milliliter of thawed ENZAR T Trypsin obtained from Intergen Co. of Purchase, N.Y., is added to 20 milliliters of distilled $H_2O$. 17 milliliters of the diluted stock is used in each application defined below. The procedure for creating the enzyme-modified combined soy/casein protein will be described first.

Because the casein has a Ph below 7, the casein must be neutralized first. Such neutralization is accomplished by combining 75 grams of New Zealand Lactic (Trademark) casein with 67.5 milliliters 1N KOH, 3.5 milliliters of 1N NaOH, and 92.5 milliliters of distilled $H_2O$. The solution is stirred to cause dispersion and is maintained at room temperature for approximately 6 minutes. Mixing is then resumed and the solution heated to 145° F., then allowed to cool to 115° F.

Next 75 grams of soy isolate obtained from Archer-Daniels of Decatur, Ill., is added to 163 milliliters of distilled $H_2O$, mixed to disperse, warmed to 145° F. and then cooled to 115° F.

The soy solution and casein solution are then combined at 115° F. in a beaker maintained at 115° F. by a water jacket. To the combination solution is add an aliquot of a chosen protease defined above, while heating to 140° F. in slightly over 5 minutes. To deactivate the particular protease, heating is then continued to 170° F., and maintained for 10 minutes.

A functional protein sol is now produced.

20 grams of K30 Povidone and 70 grams of K90 Plasdone PVP are then mixed together in 725 milliliters of distilled $H_2O$. The solution is heated to 120° F. while stirring. The protein sol is then added, with mixing for approximately 5 minutes. Once bottled, pasteurization at 190° F. for 30 minutes is desirable.

When dealing with a straight soy protein, neutralization is not necessary inasmuch as the soy protein is at an approximate 7.0 pH level.

150 grams of soy isolate is dispersed in 915 milliliters of distilled $H_2O$, and mixed while heating to 140° F. The solution is then cooled to 115° F. Next an aliquot of a chosen protease defined above is added while heating to 140° F. in slightly more than 3 minutes. Heating is then continued to 170° F. and maintained at this temperature for 10 minutes to inactivate the protease.

As described above, the compositions provide a number of advantages, some of which have been defined and others of which are inherent in the invention.

Accordingly, the scope of the invention is only to be limited as necessitated by the accompanying claims.

What is claimed is:

1. A method for producing a hydrolyzed soy protein sol comprising the steps of:

dispersing 150 grams of soy isolate in 915 milliliters of distilled $H_2O$ while heating to 140° F.;

cooling the solution to 115° F.;

adding an aliquot of a chosen protease while heating the solution to 140° F.; and heating the solution up to 170° F. and maintaining the 170° F. for 10 minutes to deactivate the protease.

2. The method of claim 1 wherein the sol is bottled and pasteurized at 190° F. for 30 minutes.

3. A method for producing a hydrolyzed combined soy/casein protein sol comprising the steps of:

combining 75 grams of casein with a 95:5 KOH/NaOH solution to neutralize the casein;

stirring at room temperature for 6 minutes;

heating the solution to 145° F.;

cooling the solution to 115° F.;

combining 75 grams of soy isolate and 163 milliliters of distilled H2O;

warming the soy solution to 145° F. and cooling down to 115° F.;

combining the soy and casein solutions at 115° F.;

adding as aliquot of a chosen protease to the combined solutions;

heating to 140° F. for approximately 5 minutes;

and heating to 170° F. and maintaining this temperature for 10 minute to deactivate the protease.

4. The method of claim 3 further including the steps of:

mixing together 20 grams of K30 Povidone and 70 grams of K90 Plasdone PVP and 725 milliliters of distilled $H_2O$;

heating the solution to 120° F. while stirring;

adding the protein sol and mixing for approximately 3 minutes;

bottling the sol and pasteurizing at 190° F.

5. A soy protein sol made by the method of claim 1.

6. A soy/casein protein sol made by the method of claim 3.

* * * * *